(12) United States Patent
Hartmann et al.

(10) Patent No.: US 6,254,829 B1
(45) Date of Patent: Jul. 3, 2001

(54) OPTOCHEMICAL SENSOR

(75) Inventors: Paul Hartmann, Weiz; Marco Jean Pierre Leiner, Graz, both of (AT)

(73) Assignee: AVL Medical Instruments, Schaffhausen (CH)

( * ) Notice: Subject to any disclaimer, the term of this patent is extended or adjusted under 35 U.S.C. 154(b) by 0 days.

(21) Appl. No.: 09/161,841

(22) Filed: Sep. 28, 1998

(30) Foreign Application Priority Data

Oct. 3, 1997 (AT) .................................................. 1678/97

(51) Int. Cl.⁷ .................................................. G01N 21/01
(52) U.S. Cl. .................. 422/82.06; 422/68.1; 422/82.05; 422/82.09; 422/82.11; 422/83; 436/127; 436/136; 436/68; 436/172
(58) Field of Search ........................... 422/55, 57, 82.05, 422/82.06; 436/68, 136, 172

(56) References Cited

U.S. PATENT DOCUMENTS

| | | | |
|---|---|---|---|
| Re. 31,879 | 5/1985 | Lubbers et al. | 436/133 |
| 3,612,866 | 10/1971 | Stevens | 21/38 |
| 4,428,859 | 1/1984 | Koch et al. | 252/301.17 |
| 4,657,736 | * 4/1987 | Marsoner et al. | 422/56 |
| 4,720,356 | 1/1988 | Chu | 252/586 |
| 4,752,115 | 6/1988 | Murray, Jr. et al. | 350/96.29 |
| 4,775,514 | 10/1988 | Barnikol et al. | 422/68 |
| 4,810,655 | 3/1989 | Khalil et al. | 436/138 |
| 4,849,172 | * 7/1989 | Yafuso et al. | 422/55 |
| 4,855,211 | 8/1989 | Janssens et al. | 430/213 |
| 5,030,420 | 7/1991 | Bacon et al. | 422/82.07 |
| 5,043,286 | 8/1991 | Khalil et al. | 436/136 |
| 5,047,350 | * 9/1991 | Switalski et al. | 436/136 |
| 5,070,158 | 12/1991 | Holloway et al. | 525/475 |
| 5,087,388 | 2/1992 | Mahoney et al. | 252/301.17 |
| 5,128,102 | 7/1992 | Kaneko et al. | 422/56 |
| 5,173,432 | * 12/1992 | Lefkowitz et al. | 436/138 |
| 5,223,380 | * 6/1993 | Mikoshiba et al. | 430/435 |
| 5,225,113 | 7/1993 | Busetto et al. | 252/586 |
| 5,242,624 | 9/1993 | Malatesta et al. | 252/586 |
| 5,242,835 | 9/1993 | Jensen | 436/136 |
| 5,380,650 | 1/1995 | Barnard et al. | 435/28 |
| 5,498,549 | * 3/1996 | Nagel et al. | 436/172 |
| 5,511,547 | 4/1996 | Markle et al. | 128/633 |
| 5,521,282 | * 5/1996 | Steinmann | 528/419 |
| 5,534,646 | * 7/1996 | Shum | 558/80 |
| 5,605,761 | * 2/1997 | Burns et al. | 428/412 |
| 5,700,077 | * 12/1997 | Dreyer, Jr. et al. | 362/32 |
| 5,714,121 | * 2/1998 | Aldrete et al. | 422/82.07 |
| 5,816,238 | * 10/1998 | Burns et al. | 126/569 |
| 5,827,880 | * 10/1998 | Malfroy-Camine et al. | 514/492 |
| 5,827,904 | * 10/1998 | Hahn | 523/113 |

FOREIGN PATENT DOCUMENTS

| | | |
|---|---|---|
| 2132348 | * 7/1984 | (GB) . |
| 9508107 | 3/1995 | (WO) . |
| 9617012 | 6/1996 | (WO) . |
| 9712227 | 4/1997 | (WO) . |

OTHER PUBLICATIONS

"Use of Tertiary Amino–groups as Substituents to Stabilise Compounds Towards Attack by Singlet Oxygen", Atkinson et al, *Journal of the Chemical Society, Perkins Transactions I*, 1973, pp. 960–964.

(List continued on next page.)

*Primary Examiner*—Jill Warden
*Assistant Examiner*—Dwayne K. Handy
(74) *Attorney, Agent, or Firm*—Baker Botts L.L.P.

(57) ABSTRACT

There is disclosed an optical sensor including a matrix containing a luminescence indicator whose luminescence may be quenched by oxygen. The optical sensor contains at least one agent capable of deactivating singlet oxygen and has an enhanced stability relative to oxygen.

22 Claims, 3 Drawing Sheets

OTHER PUBLICATIONS

"Photophysics and Photochemistry of Oxygen Sensors Based on Luminescent Transition–Metal Complexes", Carraway et al., *Analytical Chemistry*, 1991, 63, 337–442.

"Design of Oxygen Sensors Based on Quenching of Luminescent Metal Complexes: Effect of Ligand Size on Heterogeneity", Macksteder et al., *Analytical Chemistry*, 1993, 65, 3480–3483.

"Theory and Practice in Optical pH Sensing", Leiner et al., *Sensors and Actuators B*, 11(1993) 281–289.

"Optical Sensors for in Vitro Blood Gas Analysis", Leiner, *Sensors and Actuators B*, 29 (1995) 169–173.

"Formation and Removal of Singlet ($a^1\Delta_g$) Oxygen in Bulk Polymers: Events That May Influence Photodegradation", Ogilby et al., *American Chemical Society*, 1996, pp. 113–125.

\* cited by examiner

OPTOCHEMICAL SENSOR

The invention relates to an optochemical sensor including a matrix containing a luminescence indicator whose luminescence may be extinguished or quenched by oxygen.

BACKGROUND OF THE INVENTION

Optochemical sensors (optodes), in the following referred to as "optical sensors" or "sensors" for reasons of simplicity, these days are widely employed, preferably in the form of membranes, in sensor configurations in order to quantify particular substances such as, e.g., oxygen or glucose in a sample. Optical sensors are used, for instance, in environmental measuring technology and in emergency medicine (blood gas analysis). The mode of functioning of optical sensors and the basic structure of a sensor configuration generally comprising an optical sensor formed of several layers, an excitation light source and an optoelectronic detection system has been described in the literature (e.g., Sensors and Actuators B 11 (1993), pp. 281–289; Sensors and Actuators B 29 (1995), pp. 169–173).

There has already been known a plurality of indicator substances and sensors which respond to the chemical substances mentioned and, in particular, oxygen by changing an optical characteristic of the indicator. In U.S. Pat. No. 3,612,866, for instance, Stevens describes an optical sensor capable of being calibrated and sensitive to oxygen, which contains the dye pyrene, the luminescence of which is extinguished by diffusing-in oxygen in a concentration-dependent manner. At the same time, the sensor includes a reference sensor on a neighboring site, which reference sensor is masked by an additional oxygen-impermeable membrane. The concentration of oxygen is determined by the ratio of the signals of the two areas.

Furthermore, Lübbers in U.S. Reissue Pat. No. RE 31,879 describes a luminescence-optical oxygen sensor including the indicator pyrene butyric acid, optionally stirred into a silicone matrix having a high permeability for oxygen, whose sensitive layer is embedded between a light-permeable covering layer and an oxygen-permeable base layer contacted by the analyzed liquid.

In another U.S. Pat. No. 4,657,736 Marsoner describes an oxygen sensor comprising modified dyes that are readily soluble in silicone, thus offering an enhanced stability of the sensor against the aggregation of dye molecules. The sensor is prepared by stirring the dye into a prepolymer and subsequent polymerization to silicone.

In U.S. Pat. No. 4,752,115 Murray describes an oxygen-sensitive layer of a transition metal complex in a plasticized organic polymer matrix (e.g., PVC), which is applied as a layer onto a fiber optic conductor element via which the excitation light is launched. Those complexes, in general, are more photostable than organic dyes. Again, the luminescence intensity is measured as a function of the concentration of oxygen in the layer.

In U.S. Pat. No. 4,775,514 Barnikol describes a luminescent surface for determining oxygen in gases, liquids and tissues. The sensitive layer on the surface is comprised of a homogenous mixture of an organic dye (pyrene, coronene, etc.) with silicone.

Khalil in U.S. Pat. Nos. 4,810,655 and 5,043,286 describes measurements of the decay times of phosphorescent dyes having long decay times readily accessible by measuring techniques, instead of luminescence intensity measurements. The fluorinated porphyrins used exhibit relatively high photostabilities. In addition, the parameter decay time is less prone to photodecomposition effects as compared to luminescence intensity.

The same technique is employed by Bacon in U.S. Pat. No. 5,030,420, which describes an oxygen sensor comprised of a ruthenium(II) complex immobilized in a silicone that is impermeable to many liquids such as, e.g., acids and bases, complexing agents, oxidizing and reducing liquids, yet is highly permeable for oxygen and other gases. However, that sensor contains the indicator electrostatically bound to filler particles (silica gel) in the silicone, a fact the author's attention is drawn to only at a later point of time (e.g., Sacksteder, et al., Anal. Chem. 65, p. 3480). This provides for a good stability against washing out of the dye in the first place.

The stability of a sensor against washing out of the indicator also is the topic of proposals in U.S. Pat. No. 5,070,158 to Holloway and U.S. Pat. No. 5,128,102 to Kaneko, which disclose the possibility of chemically binding indicator molecules to a polymer matrix.

Another way of improving the stability of a sensor against the loss of its indicator and hence the deterioration of the photophysical properties of the membrane is set forth by Markle in U.S. Pat. No. 5,511,547. A special silicone matrix comprising polar carbinol groups serves to enhance the interaction between indicator (e.g., tris(4,7-diphenyl-1, 10-phenanthroline)ruthenium(II) chloride) and matrix in order to reduce the washing out, and also the aggregation, of the indicator molecules. Those measures are, however, not suitable for substantially enhancing the photostability of the membrane per se.

Finally, Jensen in U.S. Pat. No. 5,242,835 describes a method for determining the concentration of oxygen in a sample by detecting the emission of the singlet oxygen itself, which is excited by energy transmission during the extinction of the luminescence, occuring at a wavelength of approximately 1270 nm. Also that method is prone to photodecomposition of the indicator or the matrix by exactly that reactive singlet oxygen, the latter returning into its ground state without radiation during a photochemical reaction, thus causing also the sensitizer molecules (indicators) serving the production of the singlet oxygen to be attacked.

As already mentioned, optochemical sensors, in general, contain dyes which respond to a change in the concentration of the substance to be analyzed within the sensitive layer by changing their photophysical properties. The intensity and decay time of the luminescence of oxygen sensors will, for instance, decrease with the concentration of oxygen increasing in the sensitive layer.

A problem faced by many sensors and, in particular, oxygen sensors is their proneness to decomposition, which is triggered by the irradiated excitation light (Anal. Chem. 1991, 63, pp. 337–342). Both the luminescence indicator itself and the matrix are susceptible to decomposition. The problem of photoinduced decomposition occurs, in particular, if radiation occurs at a high intensity in order to enhance the signal quality and reduce the measuring error or if a single sensor is operated over a very long period of time as happens in the monitoring of chemical substances. Since the intensity of luminescence is a direct function of the concentration of dyes, the photodecomposition of these dyes in sensors of that kind is undesired.

The decay time of the luminescence of a sensor with dyes immobilized therein is a function of the concentration of the luminophores, in particular, if and when firstly, an overlay background luminescence (of sources other than the dye) occurs, secondly, luminescent degradation products are again formed by the photodecomposition of the dyes, the decay time of which degradation products differs from the decay time of the luminescence of the starting dyes, and thirdly, a decomposition of the matrix (environment) of the dye changes the photophysical properties of the latter.

Thus, the decomposition of the luminophore or of the matrix (for instance, by the action of singlet oxygen) of typical sensor systems is undesirable for the following reasons:

On the one hand, the mere decrease of the luminescence intensity (at a constant decay time) results in a relative increase of the background fluorescence and hence in a change of the calibration curves. The decrease of the luminescence intensity constitutes a problem to all sensor systems if the radiation quantity to be measured is thereby lowered to such an extent that the dynamic range of the receiver electronics is left. A decrease of the luminescence intensity causes particular problems to sensor systems based on the measurement of the luminescence intensity, but also to measuring systems evaluating a phase shift of the luminescence, which is caused by the finite life time of the excited states of the dye molecules.

On the other hand, a change in the luminescence decay time by photodecomposition directly leads to a change of the photophysical properties of the sensor system, this having adverse effects both on intensity measuring systems and on decay time measuring systems.

As already described above, optochemical sensors will change their photophysical properties (luminescence intensity, quantum efficiency, decay time, . . . ) in the presence of substances to be analyzed ("quencher"). The function between the concentration of the substance and the photophysical parameter, i.e., the calibration function, for instance, has the form of a Stern-Volmer equation (1), (3):

$$I_0/I = 1 + K_{SV}[Q] \quad (1a)$$

$$\tau_0/\tau = 1 + K_{SV}[Q] \quad (1b)$$

$$K_{SV} = k_q \tau_0 \quad (1c)$$

$K_{SV}$ is the Stern-Volmer constant, $k_q$ is the bimolecular deactivation rate and [Q] is the concentration of the quencher. I is the luminescence intensity and $\tau$ its decay time. The index 0 indicates the absence of a quencher.

In many cases, the decay function of the luminescence may be described by a multi-exponential model (Equ. 2).

$$i(t) = \sum_{i=1}^{m} B_i e^{-t/\tau_i} \quad (2)$$

i(t) being the time course of the emission after a comparatively short excitation pulse. $B_i$ are the amplitudes. $\tau_i$ are the time constants and m is the number of monoexponential model functions (index i), the sum of which may be described as the decay function.

In this connection, a more complex form of the Stern-Volmer equation will apply:

$$\frac{I_0}{I} = \frac{\tau_{0av}}{\tau_{av}} = \left[ \sum_{i=1}^{m} \frac{f_{0i}}{1 + K_{svi}[Q]} \right]^{-1} \quad (3)$$

$f_{0i}$ being the relative portion of the i-th decay time component. $\tau_{av}$ is a mean decay time, weighted according to the amplitudes $B_i$. The special case m=2 and $K_{SV2}$=0 is designated as a stray light model, wherein stray light may be constituted, for instance, by background fluorescence. Hence follows that the luminescence intensity and luminescence decay time must lead to a change in the parameter values of the calibration function through influences other than the present quencher as well as by a change in the stray light portion (background fluorescence).

The intensity I of luminescence is directly proportional to its quantum efficiency $\Phi_L$:

$$I = k \cdot \Phi_L \quad (4)$$

k being a proportionality constant.

The quantum efficiency, in turn, is related to the decay time via the radiating deactivation rate $k_r$ of the excited state:

$$\Phi_L = k_r \tau_0 \quad (5)$$

From the above functions it is apparent that a change in the decay time results directly in a change of the luminescence intensity (Equ. 4 and Equ. 5) and of the Stern-Volmer constant (Equ. 1c). Thus, the characteristic parameters, which are collected, for instance, by way of the calibration of a sensor by means of test substances of known compositions, will be changed, calling for the recalibration of the sensor. Frequent recalibrations, however, involve immense drawbacks if measuring is to be effected over extended period of times (monitoring). In addition, the photophysical properties of a sensor of this type may change in a manner that it will no longer offer the sensitivity required for carrying out measurements.

Such a sensor system, in general, is of the widely known optical configuration schematically represented in FIG. 1. That sensor system comprises: a light source 1 for excitation light of a suitable wavelength (matching with the absorption spectrum of the luminescence dye), a detector 2 for detecting the luminescence of the sensor 3, which is comprised of a sensitive layer 4 containing the luminescence indicator, an optical insulation layer 5 and a transparent carrier 6, filters 7, 8 for the excitation light and the emitted light, respectively, a beam splitter 9 and a measuring cell 10, which may, for instance, be a flow tube through which the sample to be assayed is transported. The transport direction of the sample is symbolized by an arrow in FIG. 1.

Measuring is effected in the following manner:

The sample to be analyzed such as, e.g., blood in which the oxygen concentration is to be determined, is transported through the flow tube 10, getting into contact with the optical insulation layer 5, which is permeable to oxygen. The oxygen gets through the optical insulation layer 5 into the sensitive layer 4, which constitutes a matrix of, for instance, a polymer containing the luminescence indicator for oxygen. The luminescence indicator is excited to luminescence by excitation light 11 coming from the light source 1, said luminescence being quenched by oxygen in a concentration-dependent manner. The emission 12 is electronically detected in the detector 2, the oxygen concentration in the sample being calculated from that value.

A light source with a time-related modulation of its intensity (pulse operation, sinus or rectangular modulation)

and a detector resolving in time, or modulated in terms of sensitivity, may be used for measuring the decay time or the phase shift. In the simplest case, the phase shift ΔΦ relative to the sinusoidally modulated light source is related to the decay time τ via the circular frequency ω of the sinus modulation:

$$tg(\Delta\Phi) = \omega\tau \tag{6}$$

Thus, also the phase shift of the sensor will change if the photodecomposition products have decay times that differ from that of the starting dye or if the environment (matrix) of the dye is influenced in a manner that the decay time changes.

All of the sensors hitherto described in the scientific literature and in the patent literature are not suitable for substantially reducing the above-mentioned photodecomposition effects. It is true that some of the above-mentioned systems are explicitly described as systems of enhanced stability, yet this may be realized to a very limited degree only by traditional measures such as the selection of a particular polymer matrix or immobilization method.

Carraway, et al. have described (Anal. Chem., 1991, 63, pp. 337–342) that the photochemical decomposition of the sensor is promoted by oxygen in oxygen sensors, but that singlet oxygen, which is formed by quenching of the excited luminescence indicator, apparently does not contribute directly to sensor decomposition and apparently is not the main cause of sensor decomposition. To stabilize oxygen sensors, those authors suggest to photolyze the sensor prior to its use in order to destroy reactive components supposed to be responsible for decomposition. Yet, also that measure is not suitable for preventing photoinduced decomposition.

SUMMARY OF THE INVENTION

It is the object of the invention to suggest an optical sensor that does not have the above-mentioned drawback and exhibits an enhanced stability against photoinduced decomposition.

The optical sensor according to the invention including a matrix containing a luminescence indicator whose luminescence may be quenched by oxygen is characterized in that the sensor comprises at least one agent capable of deactivating singlet oxygen for stabilizing the luminescence indicator and the matrix.

The invention is based on the finding that the photoinduced decomposition of sensors containing molecular oxygen in the matrix during operation, either because oxygen constitutes the analyte or—in case of a different analyte—because molecular oxygen has diffused from the sample to be analyzed into the sensor along with the analyte as an accompanying substance, in the first place is triggered by singlet oxygen and that it is feasible to effectively deactivate the singlet oxygen that is being formed in the sensor such that the photoinduced decomposition of the luminescence indicator is suppressed.

The possibility to improve particular properties and, in particular, the stability or efficiency of organic systems in connection with dyes that may be attacked by singlet oxygen has already been known and utilized in the fields of photography (photochromatic substances), laser dyes, chemiluminescence and singlet oxygen production. This is exemplified by the following publications:

Atkinson, for instance, in "Use of Tertiary Amino Groups as Substituents to Stabilise Compounds Towards Attack by Singlet Oxygen" (Journal of the Chemical Society, Perkin Transactions 1, 1973, pp. 960–964) describes the possibility to protect anthracene effectively against decomposition by singlet oxygen set in a state of excitement by methylene blue, by chemically binding a tertiary amino group to that dye via an alkyl group.

Moreover, Koch in U.S. Pat. No. 4,428,859 describes the possibility to enhance the stability of laser dyes (coumarine, xanthene, quaterphenyls, stilbenes) in nitrogen-pumped dye lasers by adding 0.01M 1,4-diazabicyclo[2,2,2]octane (DABCO).

In U.S. Pat. No. 5,087,388 Mahoney describes the stabilization of laser dyes by the controlled addition of trialkyl amines, which convert the carbonyl groups of the laser dye to less photosensitive alcohol groups and serve as radical capturers.

Furthermore, it has become known also on the photographic sector to stabilize photochromatic substances, i.e., dyes converted by light radiation thereby changing their colors, against photooxidation by singlet oxygen. Pertinent examples have been set forth by Chu in U.S. Pat. No. 4,720,356, wherein spirooxazine dyes have been supplemented with specific UV stabilizers from the class of the hindered amine light stabilizers (HALS=a sterically hindered amine used as a stabilizer against decomposition by light) as well as physical quenchers of singlet oxygen.

In U.S. Pat. No. 5,242,624 Malatesta describes the additive effect of two different light-stabilizing substances—DABCO and a HALS—in a photochromatic mixture.

In U.S. Pat. No. 5,225,113 Busetto shows that the light stabilization of photochromatic dyes functions also in thermoplastic matrices.

Finally, Janssens in U.S. Pat. No. 4,855,211 discloses that chemical groups capable of deactivating singlet oxygen may also be polymerically bound or incoporated in copolymers suitable for use in photography.

Furthermore, it is known in the field of chemiluminescence, for instance, from U.S. Pat. No. 5,380,650 to Barnard that the addition of a HALS or DABCO enhances the light efficiency of a specific chemiluminescence reaction.

Moreover, Ogilby in the article "Formation and Removal of Singlet Oxygen in Bulk Polymers: Events that May Influence Photodegradation" from the book "Polymer Durability: Degradation, Stabilization and Lifetime Prediction" (ACS Advances in Chemistry Series 249, 1995, pp. 113–126) describes the possibility of rubrene being decomposed in a polymer matrix due to the action of oxygen that has been set in the singlet state by rubrene itself through energy transmission, as well as the possibility to drastically reduce such decomposition by the addition of DABCO.

As far as Applicant knows, the use of agents for deactivating singlet oxygen in optical sensors has not been described to date.

In the present invention, substances comprising at least one amino group and, preferably, a tertiary amino group have proved to be particularly effective agents for deactivating singlet oxygen.

In addition, a hindered amine light stabilizer (HALS), a transition metal complex and, preferably, a complex of a dialkyldithiocarbamate, dialkyldithiophosphate or a Schiff's base and a transition metal ion, the optimum transition metal ions being Ni(II), Co(II), Zn(II) or Fe(III), a salt with the anions $Cl^-$, $Br^-$, $J^-$ or $NO_3^-$ or a carotenoid have proved to be particularly effective in deactivating singlet oxygen.

The agent for deactivating singlet oxygen may be contained in the matrix, i.e., present in the form of a mixture with the matrix. It may, however, also be bound to the matrix, diffusion out of the matrix, thus, being effectively prevented.

The agent may, however, also be bound to the luminescence indicator, optionally via a group —$(CH_2)_n$—, wherein n is an integer from 3 to 20. This has the advantage of providing a particularly effective protection against photodecomposition, since the agent is in the immediate vicinity of the indicator.

The matrix preferably is a polymer and, in particular, polystyrene, polyvinylchloride, plasticized polyvinylchloride, polymethylmethacrylate, plasticized polymethylmethacrylate, a polymethylmethacrylate/cellulose-acetyl-butyral mixture, a silica gel, a sol gel, a hydrogel, a silicone, poly-α-methylstyrene, a polysulfone, ethyl cellulose, cellulose triacetate, polytetrafluoroethylene, a polyester, polybutadiene, polystyrene-co-butadiene, polyurethane, polyvinylbutyral, polyethylacrylate or poly-2-hydroxyethylmethacrylate.

Also preferred are polymers which are prepared from monomers at least partially carrying an amino group and, preferably, a tertiary amino group.

DETAILED DESCRIPTION OF THE PREFERRED EMBODIMENTS

Figure 1:
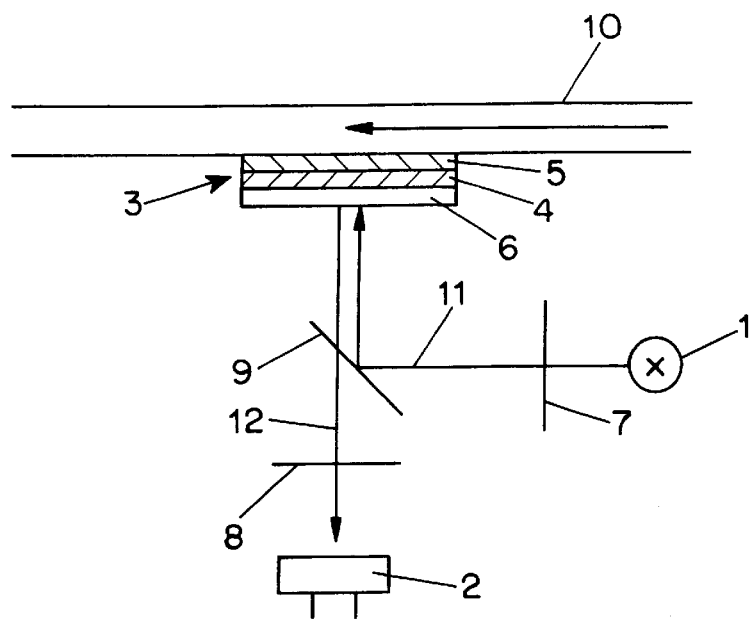
FIG. 1 is an illustration of a sensor system.

A tris-chelate complex of ruthenium(II), osmium(II), rhodium(III) or iridium(III), a metal porphyrin or a metal porphyrin ketone of platinum or palladium, a lanthanid complex of terbium, or a polycyclic aromatic hydrocarbon such as, e.g., pyrene, pyrene butyric acid and decacyclene are particularly suitable as luminescence indicators.

The invention also relates to an optical sensor configuration comprising an optical sensor, a light source for generating light for exciting the luminescence indicator and a measuring means for measuring at least one optical property of the luminescence indicator, which is characterized in that an optical sensor according to the invention is provided.

Furthermore, the invention relates to a method for determining an analyte in a gaseous or liquid sample by means of an optical sensor directly or indirectly contacted with the sample, which is characterized in that a sensor configuration according to the invention is used.

As mentioned above, the principle of the invention is applicable also to other optochemical sensors such as, e.g., pH sensors or $pCO_2$ sensors, provided reactive oxygen may form also in those sensors. The widely known pH-sensitive indicator 1-hydroxy-pyrene-3,6,8-trisulfonate (HPTS), for instance, exhibits a significant cross sensitivity to oxygen (cf. Leiner, Sensors and Actuators B 11, 281–289, 1993), which also has a negative effect on the photostability of the indicator.

Within the sensor, a singlet state of the molecular oxygen "singlet oxygen" may develop from a collision complex between an indicator molecule and molecular oxygen, which is in the state of excitement, by the transmission of energy from the indicator molecule, which singlet oxygen, after diffusive separation of the collision complex, returns into the ground state either without radiation or while emitting radiation at a wavelength of 1270 nm, or is deactivated by the polymer matrix without radiation, or causes a chemical reaction and hence a conversion of the indicator, or causes a chemical reaction with the matrix, thus changing the molecular environment of the dye. That extremely reactive singlet oxygen may, however, be deactivated also according to the invention by the stabilizing additives admixed, either by energy transfer, charge transfer or a chemical reaction (or by combinations of these mechanisms), thus no longer endangering the sensor.

When selecting the agents or additives, it should be safeguarded in all of the embodiments that the substances added do not create a strong background luminescence or do not substantially alter the photophysical properties or even the chemical consistency of the indicator so as to no longer guarantee the function of the sensor. Moreover, a high volatility of the substances added would undo the advantages of stabilization, in particular if the photophysical properties of the indicator were influenced by the substance added, which properties would also change with a changing concentration of the substance added.

The following examples of negative influences of additives on the photophysical properties of certain sensor types may be given:

1. Oxygen sensors comprised of the indicator tris(4,7-diphenyl-1,10-phenanthroline)ruthenium(II) perchlorate, which is present at a concentration of 5 mM in a polystyrene matrix in a homogenously dissolved state, are rendered practically unusable by the addition of 1% by weight of bis-(tetraethylammonium)-bis-(dimercaptomaleonitrilato)-nickelate(II), a singlet oxygen quencher, since the additive also extinguishes the luminescence of the ruthenium complex to the major extent.

2. The photostability of oxygen sensors comprised of the indicator tris(4,7-diphenyl-1,10-phenanthroline) ruthenium(II) perchlorate, which is present at a concentration of 5 mM in a polystyrene matrix in a homogenously dissolved state, is substantially deteriorated by the addition of 1% by weight of 3,5-N,N-tetramethylaniline, this additive very effectively reducing ruthenium complexes.

3. The photostability of oxygen sensors comprised of the indicator tris(4,7-diphenyl-1,10-phenanthroline) ruthenium(II) perchlorate, which is present at a concentration of 5 mM in a polystyrene matrix in a homogenously dissolved state, is substantially deteriorated by the addition of 1% by weight of various phenols (Irganox 245, Irganox 1076, BHT, etc.). Phenolic antioxidants primarily serve to protect polymers against photooxidation, yet in the chemical reaction chain thus activated radicals of the antioxidants occur, which, in turn, may attack the ruthenium complexes.

The favorable action of the present invention is going to be demonstrated by way of the following Example.

EXAMPLE

The cyclic amine 1,4-diazabicyclo[2,2,2]octane (DABCO) at a concentration of, for instance, 90 mM is incorporated in an oxygen sensor comprising the luminescence indicator tris(4,7-diphenyl- 1,10-phenanthroline) ruthenium(II) perchlorate, which is present at a concentration of 5 mM in a polystyrene matrix in a homogenously dissolved state: 2 g polystyrene are dissolved in 15 ml methyl ethyl ketone, 13.5 mg of the ruthenium indicator and 20 mg DABCO are weighed in and dissolved by stirring. The solution is applied onto a carrier (mylar, glass, etc.) as a thin layer by known methods such as, for instance, doctoring or spin-coating. The solvent is evaporated.

The carrier, at the same time, serves to protect the sensitive layer of the sensor membrane against any undesired action by oxygen from the environment of the membrane. Optionally, an optical insulation layer of an oxygen-permeable material may also be applied in order to optically decouple the sample from the sensor.

For reasons of comparison, a similar layer is prepared by omitting DABCO.

Figure 2:
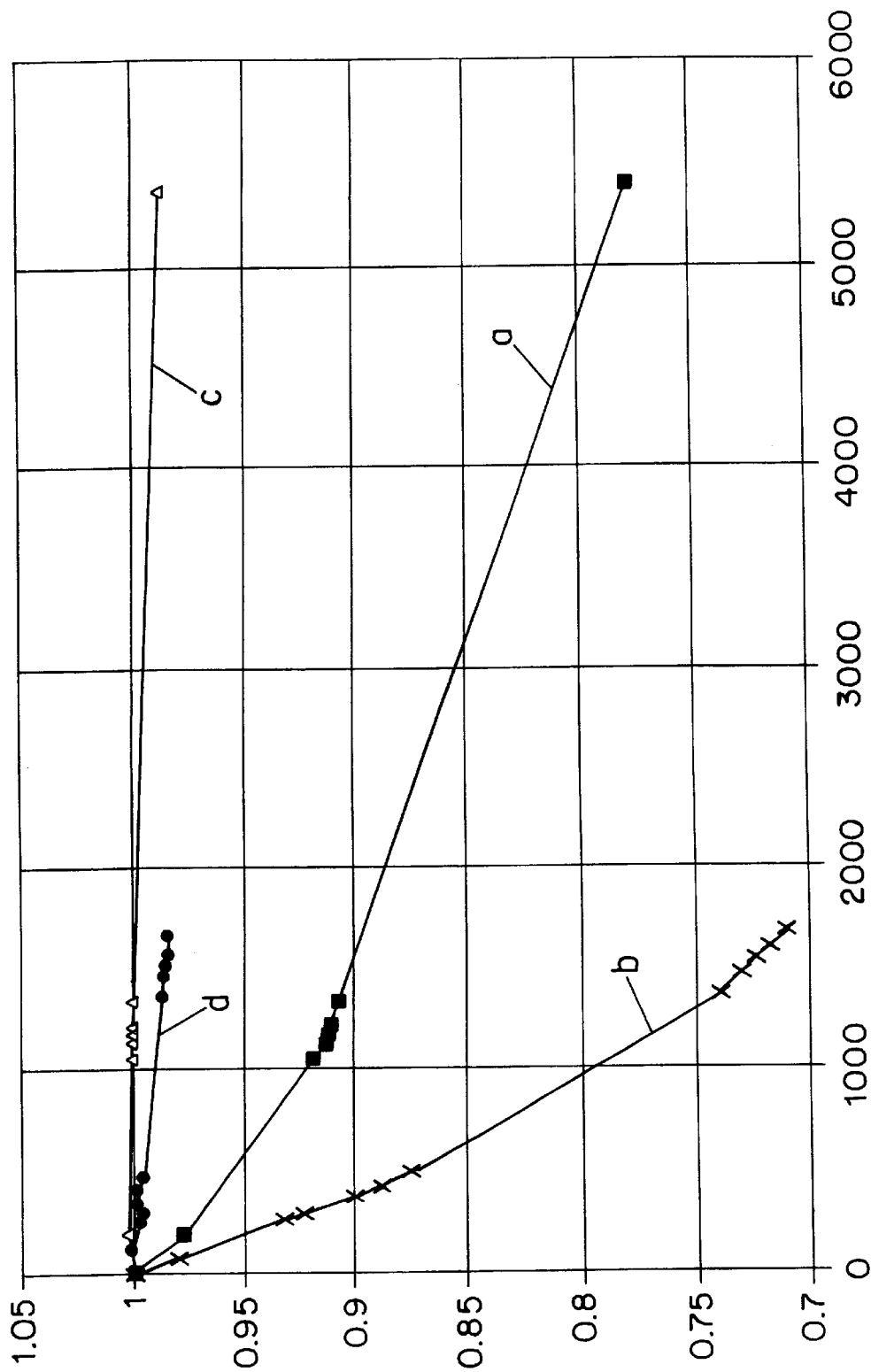
FIG. 2 is a graph of fluorescence intensity versus illumination time.

FIG. 2 is a diagram in which the relative decreases of the luminescence intensity and the phase shift $\Delta\Phi$ (Equ. 6) during the illumination of the sensor with blue light (central wavelength 470 nm of a Nichia NSPB500 LED) having the intensity $E_e=20$ mW/cm$^2$ at T=37° C. under ambient air are plotted on the ordinate. The illumination time in minutes is indicated on the abscissa.

For reasons of comparison, measuring data both of the sensor containing DABCO (relative intensity: curve a; relative phase shift: curve c) and of the sensor free of DABCO (relative intensity: curve b; relative phase shift: curve d) are represented in the diagram and in the table. As is apparent from the diagram, both the relative phase shift (decay time) and—to a larger extent—the relative luminescence intensity are affected by the effect of photobleaching.

Figure 3:
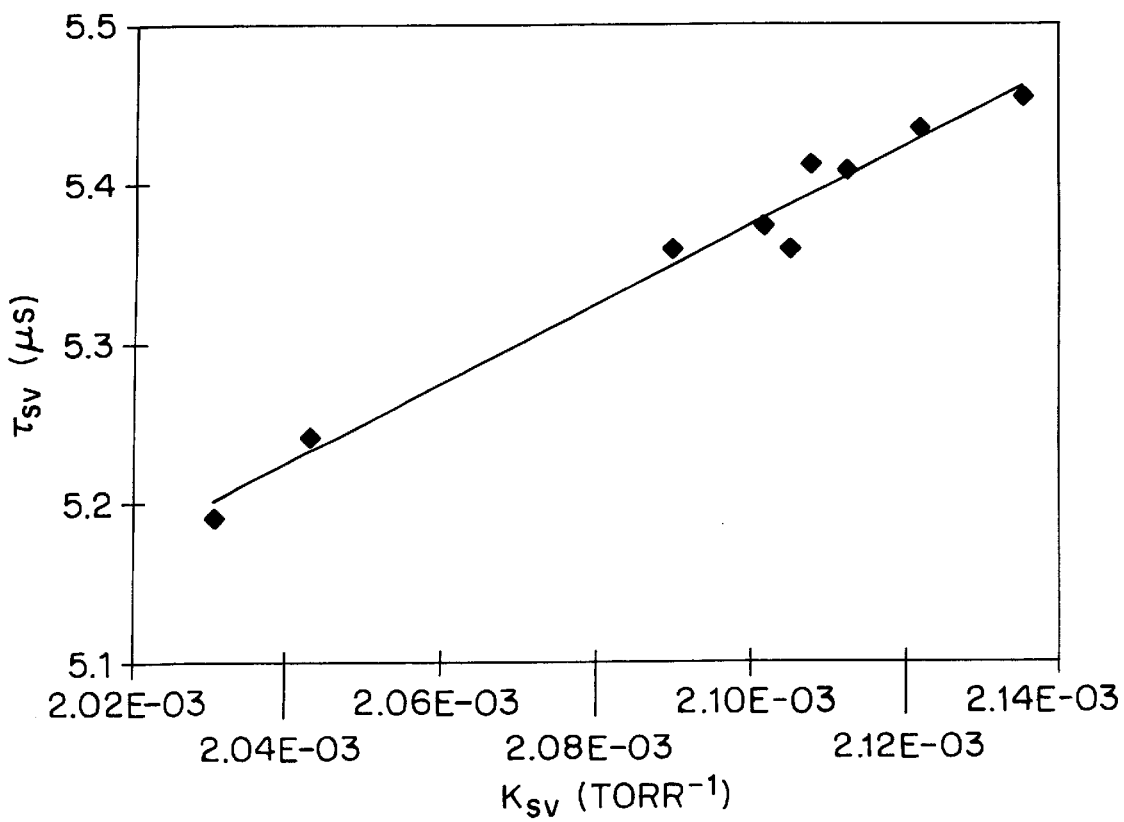
FIG. 3 is a graph of decay time versus Stern-Vollmer constant.

Likewise, it is possible to detect a reduction of the Stern-Volmer constant parallel with the reduction of the decay time (FIG. 3). Oxygen strongly favors photodegeneration, yet there might also be a thermal influence (in the absence of oxygen). DABCO addition in the first place substantially lowers the effect of photobleaching by physically quenching singlet oxygen (cf. table). The table also includes measuring data obtained by using other additives. The bleaching effect is quantified as the relative signal reduction (intensity reduction $\Delta I_{16}$, change in the phase shift $\Delta\Phi_{16}$) after 16 hours of illumination under pure oxygen and the remaining conditions pointed out above.

Figure 4:
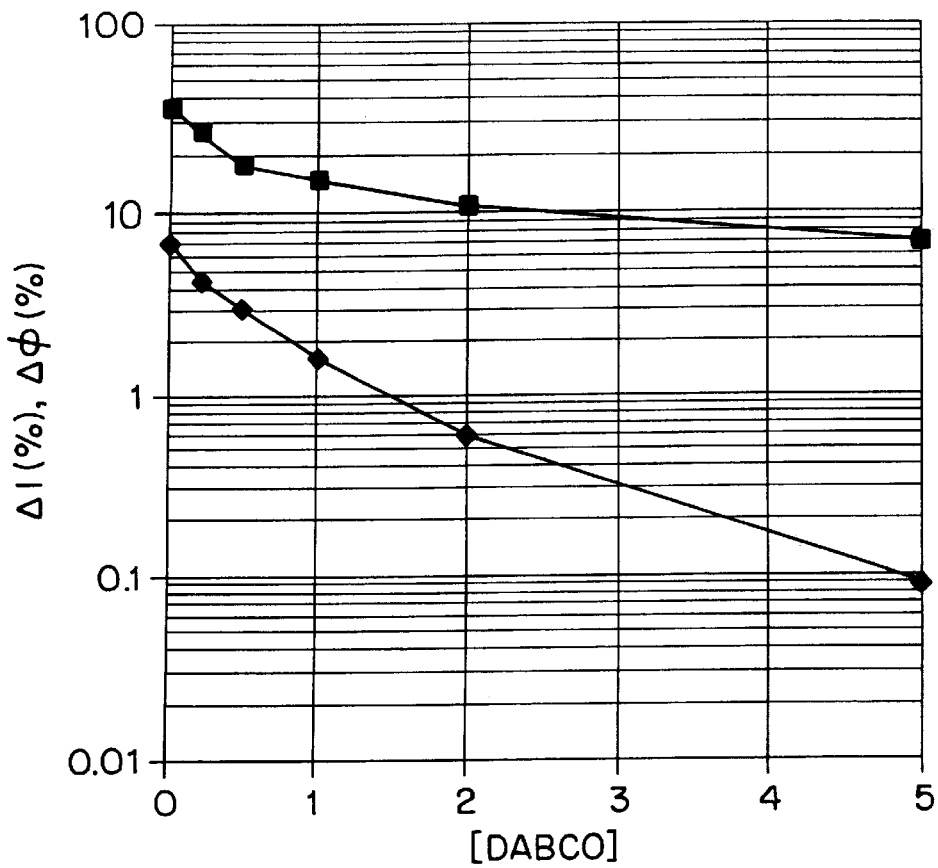
FIG. 4 is a graph of change in intensity versus concentration of 1,4-diazabicyclo[2,2,2]octane.

The effects of additives such as DABCO depend on the concentrations of the same in the sensitive layer. FIG. 4 illustrates the concentration dependence (abscissa: weight % DABCO) of stabilization.

Figure 5:
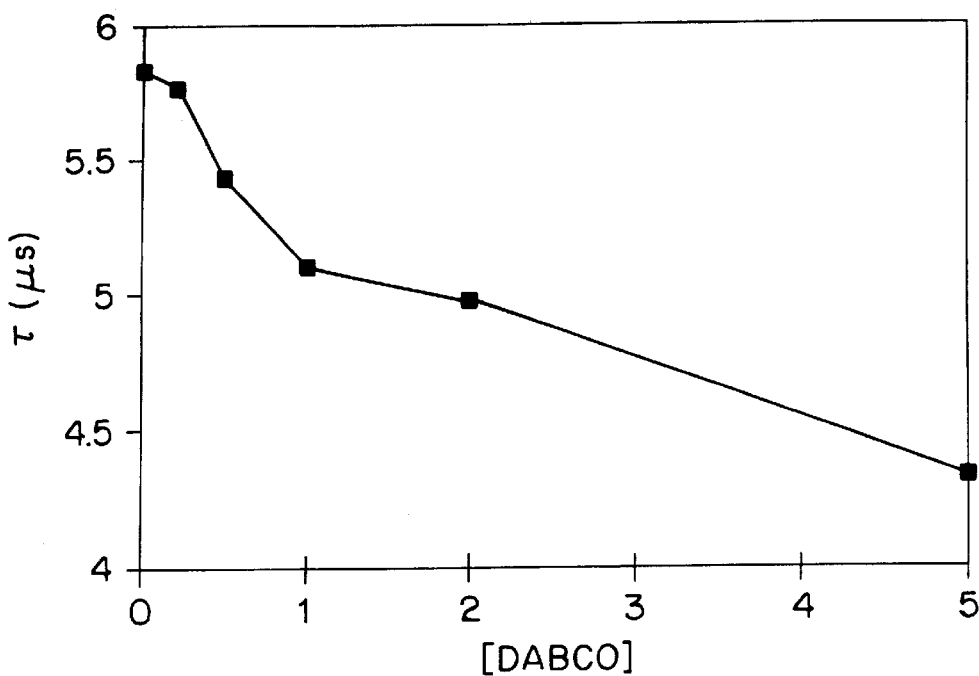
FIG. 5 is a graph of decay time versus concentration of 1,4-diazabicyclo[2,2,2]octane.

Many of the additives contemplated, and also DABCO, have the side effect of influencing the photophysical properties of the indicator in the sensitive layer. FIG. 5 shows the decrease of the decay time with the concentration of DABCO increasing (abscissa: weight % DABCO): This effect is, however, not very great in the instant case as compared to the effect of stabilization, thus jeopardizing neither the effectiveness of the additive against photodecomposition nor the sensitivity of the sensor.

Similarly good results could be obtained by replacing the sensor mentioned in the Example with the following sensors: tris(1,10-phenanthroline)ruthenium(II)/PVC/DABCO; tris(4,7-diphenyl-1,10-phenanthroline)ruthenium(II)/plasticized PVC/DABCO; tris(1,10-phenanthroline) ruthenium(II)/silica gel in silicone/DABCO; tris(2,2'-bipyridyl)ruthenium(II)/silica gel in silicone/DABCO; tris (4,7-diphenyl-1,10-phenanthroline)ruthenium(II)/polystyrene/Chimassorb 944; tris(4,7-diphenyl-1,10-phenanthroline)ruthenium(II)/polystyrene/DABCO+ Chimassorb 944; tris(4,7-diphenyl-1,10-phenanthroline) ruthenium(II)/polystyrene/Tinuvine 770; tris(4,7-diphenyl-1,10-phenanthroline)ruthenium(II)/poly-(4-(N,N-dimethylamino)-styrene); tris(4,7-diphenyl-1,10-phenanthroline)ruthenium(II)/poly-(4-(N,N-dimethylamino)-styrene)-co-poly-styrene (97%); platinum (II)-octaethylporphyrin/polystyrene/DABCO; platinum(II)-octaethylporphyrin ketone/polystyrene/DABCO; platinum (II)-octaethylporphyrin ketone/PVC/Ni-chelate.

Table

Relative change in intensity and relative change in phase shift of the luminescence of tris(4,7-diphenyl-1,10-phenanthroline)ruthenium perchlorate in polystyrene after 16 hours of illumination with blue light (470 nm) at an intensity of 20 mW/cm$^2$. Sensor temperature T=37° C.; bleaching under oxygen measuring under nitrogen. Untreated sensor vs. variants upon addition of stabilizing additives.

| Additive | $\Delta I_{16}$ % | $\Delta\Phi_{16}$ % |
|---|---|---|
| — | 35 | 6.6 |
| 1% DABCO | 14 | 1.6 |
| 1% Chimassorb 944 | 18 | 35 |
| 1% DABCO + 1% Chimassorb 944 | 10 | 1.2 |
| 1% Tinuvine 770 | 19 | 42 |

What is claimed is:

1. An optical sensor configuration comprising:
   an optical sensor including a polymer matrix, the matrix including a luminescence indicator contained in said matrix wherein said optical sensor comprises at least one agent capable of deactivating singlet oxygen, and a transparent carrier,
   a light source for exciting the luminescence indicator, and
   a detector for determining at least one optical property of said luminescence indicator in the presence of a sample.

2. An optical sensor configuration as set forth in claim 1, wherein said agent capable of deactivating singlet oxygen comprises at least one amino group.

3. An optical sensor configuration as set forth in claim 2, wherein said amino group is a tertiary amino group.

4. An optical sensor configuration as set forth in claim 1, wherein said agent capable of deactivating singlet oxygen is a hindered amine light stabilizer (HALS).

5. An optical sensor configuration as set forth in claim 1, wherein the agent capable of deactivating singlet oxygen is a transition metal complex.

6. An optical sensor configuration as set forth in claim 5, wherein said transition metal complex is a complex of a dialkyldithio carbamate and a transition metal ion.

7. An optical sensor configuration as set forth in claim 5, wherein said transition metal complex is a complex of a dialkyldithio phosphate and a transition metal ion.

8. An optical sensor configuration as set forth in claim 5, wherein said transition metal complex is a complex of a Schiff's base and a transition metal ion.

9. An optical sensor configuration as set forth in claim 6, 7 or 8, wherein the transition metal ion is selected from the group consisting of Ni(II), Co(II), Zn(II) and Fe(III).

10. An optical sensor configuration as set forth in claim 1, wherein the agent capable of deactivating singlet oxygen is a salt with an anion selected from the group consisting of Cl$^-$, Br$^-$, I and NO$_3^-$.

11. An optical sensor configuration as set forth in claim 1, wherein said agent capable of deactivating singlet oxygen is a carotenoid.

12. An optical sensor configuration as set forth in claim 1, wherein said agent capable of deactivating singlet oxygen is contained in said matrix.

13. An optical sensor configuration as set forth in claim 1, wherein said agent capable of deactivating singlet oxygen is bound to said matrix.

14. An optical sensor configuration as set forth in claim 1, wherein said agent capable of deactivating singlet oxygen is bound to said luminescence indicator.

15. An optical sensor configuration as set forth in claim 14, wherein said agent capable of deactivating singlet oxygen is bound to said luminescence indicator via a group —$(CH_2)_n$—, wherein n is an integer from 3 to 20.

16. An optical sensor as set forth in claim 1, wherein said polymer is selected from the group consisting of polystyrene, polyvinylchloride, plasticized polyvinylchloride, polymethylmethacrylate, plasticized polymethylmethacrylate, a polymethylmethacrylate/cellulose-acetyl-butyral mixture, a silica gel, a sol gel, a hydrogel, a silicone, poly-α-methylstyrene, a polysulfone, ethyl cellulose, cellulose triacetate, polytetrafluoroethylene, a polyester, polybutadiene, polystyrene-co-butadiene, polyurethane, polyvinylbutyral, polyethylacrylate and poly-2-hydroxyethylmethacrylate.

17. An optical sensor as set forth in claim 1, wherein said polymer is prepared of monomers at least partially carrying an amino group.

18. An optical sensor as set forth in claim 17, wherein said amino group is a tertiary amino group.

19. An optical sensor as set forth in claim 1, wherein said luminescence indicator is selected from the group consisting of a tris-chelate complex of ruthenium(II), a tris-chelate complex of osmium(II), a tris-chelate complex of rhodium (III), a tris-chelate complex of iridium(III), a metal porphyrin of platinum, a metal porphyrin ketone of platinum, a metal porphyrin of palladium, a metal porphyrin ketone of palladium, a lanthanid complex of terbium and a polycyclic aromatic hydrocarbon.

20. An optical sensor comprising:

an optical sensor including a polymer matrix, a luminescence indicator contained in said matrix wherein said matrix comprises at least one agent capable of deactivating singlet oxygen, and a transparent carrier.

21. A method for determining an analyte in a gaseous liquid or sample which method comprises:

providing an optical sensor including a polymer matrix, a luminescence indicator contained in said matrix and exhibiting a luminescence capable of being quenched by oxygen thus forming singlet oxygen, and at least one agent capable of deactivating singlet oxygen for stabilizing said luminescence indicator and said matrix, providing a light source for generating light for exciting said luminescence indicator, directly contacting said sample with said sensor, and providing measuring means for measuring at least one optical property of said luminescence indicator.

22. A method for determining an analyte contained in a gaseous sample, which method comprises:

providing an optical sensor including a polymer matrix, a luminescence indicator contained in said matrix and exhibiting a luminescence capable of being quenched by oxygen thus forming singlet oxygen, and at least one agent capable of deactivating singlet oxygen for stabilizing said luminescent indicator and said matrix, and a transparent carrier, providing a light source for generating light for exciting said luminescence indicator, indirectly contacting said sample with said sensor and determining the presence of the analyte, and providing measuring means for measuring at least one optical property of said luminescence indicator.

* * * * *